US008487138B2

(12) United States Patent
Dakka et al.

(10) Patent No.: US 8,487,138 B2
(45) Date of Patent: Jul. 16, 2013

(54) OXIDATION OF HYDROCARBONS

(75) Inventors: Jihad M. Dakka, Whitehouse Station, NJ (US); James C. Vartuli, West Chester, PA (US); Stephen Zushma, Clinton, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 368 days.

(21) Appl. No.: 12/601,549

(22) PCT Filed: Jul. 11, 2008

(86) PCT No.: PCT/US2008/069779
§ 371 (c)(1),
(2), (4) Date: May 28, 2010

(87) PCT Pub. No.: WO2009/025939
PCT Pub. Date: Feb. 6, 2009

(65) Prior Publication Data
US 2010/0234589 A1  Sep. 16, 2010

Related U.S. Application Data

(60) Provisional application No. 60/957,250, filed on Aug. 22, 2007.

(51) Int. Cl.
C07C 45/00 (2006.01)
C07C 309/00 (2006.01)
C07C 37/08 (2006.01)
C07C 51/16 (2006.01)

(52) U.S. Cl.
USPC ........... 568/314; 568/346; 568/351; 568/385; 568/560; 568/768

(58) Field of Classification Search
USPC .......................................... 568/314, 346, 351
See application file for complete search history.

(56) References Cited

U.S. PATENT DOCUMENTS

| | | |
|---|---|---|
| 3,418,256 A | 12/1968 | Rigney et al. |
| 3,959,381 A | 5/1976 | Arkell et al. |
| 4,136,123 A | 1/1979 | Hutchings |
| 4,255,592 A | 3/1981 | Kawai et al. |
| 4,282,383 A | 8/1981 | Dai et al. |
| 4,450,303 A | 5/1984 | Drake |
| 5,030,739 A | 7/1991 | Foricher et al. |
| 5,166,454 A | 11/1992 | Harandi et al. |
| 5,298,667 A | 3/1994 | Iwanaga et al. |
| 5,405,814 A | 4/1995 | Beech, Jr. et al. |
| 5,981,420 A | 11/1999 | Nakano et al. |
| 6,291,718 B1 | 9/2001 | Matsui et al. |
| 6,528,658 B1 | 3/2003 | Miura et al. |
| 6,720,462 B2 | 4/2004 | Kuhnle et al. |
| 6,852,893 B2 | 2/2005 | Kuhnle et al. |
| 7,038,089 B2 | 5/2006 | De Frutos Escrig et al. |
| 7,326,815 B2 | 2/2008 | Dakka et al. |
| 2002/0169331 A1 | 11/2002 | Miura et al. |
| 2003/0083527 A1 | 5/2003 | Kuhnle et al. |
| 2004/0014985 A1 | 1/2004 | Sugahara |
| 2004/0162448 A1 | 8/2004 | Yang et al. |

(Continued)

FOREIGN PATENT DOCUMENTS

| | | |
|---|---|---|
| DE | 2 300 903 | 1/1973 |
| EP | 1 074 536 | 2/2001 |

(Continued)

OTHER PUBLICATIONS

Ishii, Y. et al. "*Recent Progress in Aerobic Oxidation of Hydrocarbons by N-hydroxyimides*" Catalysis Today, 2006, vol. 117, pp. 105-113.

J. Howard et al., "*Absolute Rate Constants for Hydrocarbon Oxidation. XI. The Reactions of Tertiary Peroxy Radicals*[1,2]", Canadian Journal of Chemistry, 1968, vol. 47, pp. 2656-2660.

J. Howard et al., "*Absolute Rate Constants for Hydrocarbon Oxidation. VIII. The Reactions of Cumylperoxy Radicals*[1]", Canadian Journal of Chemistry, 1968, vol. 46, pp. 1018-1022.

J. Howard, "*Absolute Rate Constants for Hydrocarbon Autoxidation. XXII. The Autoxidation of Some Vinyl Compounds*[1]", Canadian Journal of Chemistry, 1972, vol. 50, pp. 2298-2304.

(Continued)

*Primary Examiner* — Shawquiz Young
(74) *Attorney, Agent, or Firm* — Anthony G. Boone; Jamie L. Sullivan; Siwen Chen

(57) ABSTRACT

In a process for oxidizing a hydrocarbon to a corresponding hydroperoxide, alcohol, ketone, carboxylic acid or dicarboxylic acid, the hydrocarbon is contacted with an oxygen-containing gas in the presence of a catalyst comprising a cyclic imide of the general formula (I):

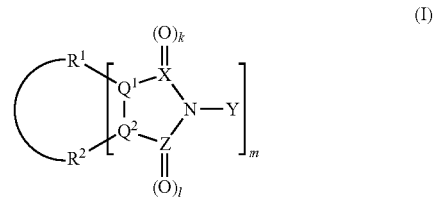

(I)

wherein each of $R_1$ and $R_2$ is independently selected from hydrocarbyl and substituted hydrocarbyl radicals having 1 to 20 carbon atoms, or from the groups $SO_3H$, $NH_2$, $OH$ and $NO_2$, or from the atoms H, F, Cl, Br and I provided that $R_1$ and $R_2$ can be linked to one another via a covalent bond; each of $Q^1$ and $Q^2$ is independently selected from C, CH, N and $CR^3$; each of X and Z is independently selected from C, S, $CH_2$, N, P and an element of Group 4 of the Periodic Table; Y is O or OH; k is 0, 1, or 2; 1 is 0, 1, or 2; m is 1 to 3, and $R^3$ can be any of the entities listed for $R^1$. The contacting produces an effluent comprising an oxidized hydrocarbon product and unreacted imide catalyst of formula (I) and the effluent is treated with an aqueous solution of a base to produce an aqueous phase comprising at least part of the unreacted imide catalyst of formula (I) and an organic phase comprising oxidized hydrocarbon product. The organic phase can then be recovered.

24 Claims, 2 Drawing Sheets

U.S. PATENT DOCUMENTS

| | | |
|---|---|---|
| 2004/0236152 A1 | 11/2004 | Black et al. |
| 2005/0043559 A1 | 2/2005 | Marhold et al. |
| 2005/0167658 A1 | 8/2005 | Williams et al. |
| 2007/0265476 A1 | 11/2007 | Dakka et al. |
| 2008/0269507 A1 | 10/2008 | Kajikawa et al. |
| 2010/0222609 A1 | 9/2010 | Dakka et al. |

FOREIGN PATENT DOCUMENTS

| | | |
|---|---|---|
| EP | 1 088 807 | 4/2001 |
| EP | 1 088 809 | 4/2001 |
| JP | 62-114922 | 5/1987 |
| JP | 11-180913 | 7/1999 |
| JP | 2001-192354 | 7/2001 |
| JP | 2002-282698 | 10/2002 |
| JP | 2004/035460 | 5/2004 |
| WO | 94/20213 | 9/1994 |
| WO | 99/47485 | 9/1999 |
| WO | 2006/015826 | 2/2006 |
| WO | 2008/037435 | 4/2008 |
| WO | 2009/025939 | 2/2009 |
| WO | 2010/098916 | 9/2010 |

OTHER PUBLICATIONS

J. Howard et al., "*Absolute Rate Constants for Hydrocarbon Autoxidation. XV. The Induced Decomposition of Some T-Hydroperoxides[1]*", Canadian Journal of Chemistry, 1969, vol. 47, pp. 3797-3801.

J. Howard et al., "*Absolute Rate Constants for Hydrocarbon Autoxidation. XIV. Termination Rate Constants for Tertiary Peroxy Radicals[1]*", Canadian Journal of Chemistry, 1969, vol. 47, pp. 3793-3795.

T. Iwahama et al., "*Aerobic Oxidation of Alcohols to Carbonyl Compounds Catalyzed by N-Hydroxyphthalimide (NHPI) Combined with Co (acac)$_3$*", Tetrahedron Letters, 1995, vol. 36, No. 38, pp. 6923-6926.

J. Kochi, "*Chemistry of Alkoxy Radicals: Cleavage Reactions*", Journal of the American Chemical Society, 1962, vol. 84, pp. 1193-1197.

S. Sakaguchi et al., "*Oxidation of Organic Substrates with Molecular Oxygen Catalyzed by Vanadomolybdophosphate (NPV$_6$Mo$_6$) Combined with N-Hydroxyphthalimide (NHPI)*", Technology Reports of Kansai University, 1996, No. 38, pp. 123-131.

R. Sheldon et al., "*Organocatalytic Oxidations Mediated by Nitroxyl Radicals*", Advanced Synth. Catal., 2004, vol. 346, pp. 1051-1071.

Y. Yen, "*Phenol*", Process Economics Report No. 22B, Stanford Research Institute, 1977, pp. 113-121, 261 and 263.

OXIDATION OF HYDROCARBONS

CROSS REFERENCE TO RELATED APPLICATIONS

This application is a National Stage Application of International Application No. PCT/US2008/069779 filed Jul. 11, 2008, which claims priority from U.S. Ser. No. 60/957,250 filed Aug. 22, 2007, both of which are incorporated herein by reference.

FIELD

The present invention relates to a process for oxidizing hydrocarbons and, in particular, alkylaromatic hydrocarbons to produce for example phenol and substituted phenols.

BACKGROUND

The oxidation of hydrocarbons is an important reaction in industrial organic chemistry. Thus, for example, the oxidation of cyclohexane is used commercially to produce cyclohexanol and cyclohexanone, which are important precursors in the production of nylon, whereas oxidation of alkylaromatic hydrocarbons is used to produce phenol, a precursor in the production of polycarbonates and epoxy resins.

Oxidation of hydrocarbons can be conducted using well-known oxidizing agents, such as $KMnO_4$, $CrO_3$ and $HNO_3$. However, these oxidizing agents have the disadvantage of being relatively expensive, and moreover their use is accompanied by the production of unwanted coupling products which can represent disposal problems and ecological pollution.

Preferably, therefore, oxidizing agents based on peroxides or $N_2O$ are used. The cheapest oxidizing agent, however, is molecular oxygen, either in pure form or as atmospheric oxygen. However, oxygen itself is usually unsuitable for oxidizing hydrocarbons, since the reactivity of the $O_2$ molecule, which occurs in the energetically favorable triplet form, is not sufficient.

By using redox metal catalysts it is possible to utilize molecular oxygen for oxidizing organic compounds and hence a great number of industrial processes are based on the metal-catalyzed autooxidation of hydrocarbons. Thus, for example, the oxidation of cyclohexane with $O_2$ to cyclohexanol and/or cyclohexanone proceeds with the use of cobalt salts. These industrial processes are based on a free-radical chain mechanism, in which the bi-radical oxygen reacts with a hydrocarbon free radical, with formation of a peroxy radical and subsequent chain propagation by abstraction of an H atom from a further hydrocarbon. In addition to metal salts, however, organic molecules can also act as free-radical initiators.

However, it is a disadvantage of these processes that the selectivity decreases very greatly with increasing conversion and therefore the processes must be operated at a very low level of conversion. Thus, for example, the oxidation of cyclohexane to cyclohexanol/cyclohexanone is carried out at a conversion of 10 to 12% so that the selectivity is 80 to 85% ("Industrielle Organische Chemie" [Industrial Organic Chemistry] 1994, 261, VCH-Verlag, D-69451 Weinheim).

An alternative to metal salt catalysts is the use of organic mediators, for example N-hydroxyphthalimide (NHPI). Thus, U.S. Pat. Nos. 6,852,893 and 6,720,462 describe methods for oxidizing hydrocarbon substrates by contacting the substrate with an oxygen-containing gas, in which the oxygen content is from 5 to 100% by volume, in the presence of a free radical initiator and a catalyst, typically an N-hydroxycarbodiimide catalyst, such as N-hydroxyphthalimide (NHPI). The process is conducted at a temperature between 0° C. and 500° C. and a pressure between atmospheric and 100 bar (100 and 10,000 kPa). The molar ratio of the catalyst to the hydrocarbon substrate can range from $10^{-6}$ mol % to 1 mol %, whereas the molar ratio of free-radical initiator to the catalyst can be 4:1 or less, such as 1:1 to 0.5:1. Suitable substrates that may be oxidized by this process include cumene, cyclohexylbenzene, cyclododecylbenzene and sec-butylbenzene.

U.S. Pat. No. 7,038,089 discloses a process for preparing a hydroperoxide from a hydrocarbon selected from a group consisting of primary hydrocarbons, secondary hydrocarbons and mixtures thereof corresponding to said hydroperoxide which comprises conducting oxidation of said hydrocarbon at a temperature in the range between 130 and 160° C. with an oxygen-containing gas in a reaction mixture containing said hydrocarbon and a catalyst comprising a cyclic imide compound and an alkali metal compound. Suitable hydrocarbons are said to include $C_4$ to $C_{20}$ tertiary alkanes (e.g., iso-butane, iso-pentane, iso-hexane, and the like), $C_7$ to $C_{20}$ (alkyl) aromatic hydrocarbons with 1 to 6 aromatic rings or $C_9$ to $C_{20}$ (cycloalkyl) aromatic hydrocarbons with 1 to 6 aromatic rings (e.g., xylene, cumene, cumene, ethylbenzene, diisopropylbenzene, cyclohexylbenzene, tetrahydronaphthalene (tetraline), indan, etc.), and the like. The amount of the cyclic imide compound used may be from 0.0001 to 1%, preferably from 0.0005 to 0.5%, by weight based on the reaction mixture, whereas the amount of the alkali metal compound may be from 0.000005 to 0.01%, preferably from 0.00001 to 0.005%, by weight based on the reaction mixture However, although current work has continued to demonstrate the utility of cyclic imides as hydrocarbon oxidation catalysts, it has also shown that their application in a commercial process requires further investigation. In particular, cyclic imides, such as N-hydroxyphthalimide, are expensive and are readily hydrolyzed under the conditions of the oxidation reaction. Moreover, unreacted imide catalysts and their decomposition products (acids and ethers) can pose significant problems to the downstream reactions, such as hydroperoxide cleavage. Thus the successful application of cyclic imides to the oxidation of hydrocarbons will require treatment of the oxidation effluent to remove unreacted imides and their decomposition products and, if possible, recovery and recycle of the valuable unreacted imides.

According to the invention, it has now been found that unreacted imide catalyst and its decomposition products can be at least partially removed from the effluent of the catalytic oxidation of hydrocarbons by treatment of the effluent with an aqueous solution of a base and particularly, a weak base, such as metal carbonate and/or hydrogen carbonate. The unreacted imide is extracted into the aqueous phase leaving an organic phase that is essentially free of the imide species. By subsequently acidifying the aqueous phase, the imide species can be precipitated and recovered for recycle to the oxidation step.

SUMMARY

In one aspect, the present invention resides in a process for oxidizing a hydrocarbon to a corresponding hydroperoxide, alcohol, ketone, carboxylic acid or dicarboxylic acid, the process comprising (a) contacting a hydrocarbon with an oxygen-containing gas in the presence of a catalyst comprising a cyclic imide of the general formula (I):

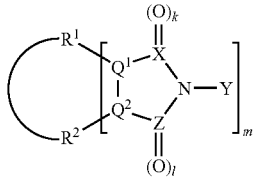

(I)

wherein each of $R^1$ and $R^2$ is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I, provided that $R^1$ and $R^2$ can be linked to one another via a covalent bond;
each of $Q^1$ and $Q^2$ is independently selected from C, CH, N and $CR^3$;
each of X and Z is independently selected from C, S, $CH_2$, N, P and elements of Group 4 of the Periodic Table;
Y is O or OH;
k is 0, 1, or 2;
l is 0, 1, or 2,
m is 1 to 3; and
$R^3$ can be any of the entities (radicals, groups, or atoms) listed for $R^1$; and
wherein said contacting produces an effluent comprising an oxidized hydrocarbon product and unreacted imide catalyst of said formula (I);

(b) treating the effluent with an aqueous solution of a base to produce an aqueous phase comprising at least part of said unreacted imide catalyst of said formula (I) and an organic phase comprising said oxidized hydrocarbon product; and (c) recovering said organic phase.

Conveniently, said hydrocarbon is an alkane or cycloalkane, such as isobutane or cyclohexane.

Alternatively, said hydrocarbon is an alkylaromatic compound of general formula (II):

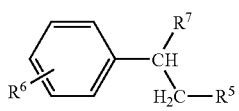

(II)

wherein $R^4$ and $R^5$ each independently represents hydrogen or an alkyl group having from 1 to 4 carbon atoms, provided that $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group.

Conveniently, said alkylaromatic compound of general formula (II) is selected from ethyl benzene, cumene, sec-butylbenzene, sec-pentylbenzene, p-methyl-sec-butylbenzene, 1,4-diphenylcyclohexane, sec-hexylbenzene, and cyclohexylbenzene.

Conveniently, said cyclic imide obeys the general formula (III):

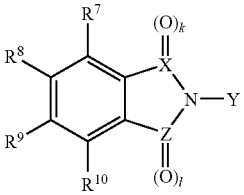

(III)

wherein each of $R^7$, $R^8$, $R^9$, and $R^{10}$ is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I;
each of X and Z is independently selected from C, S, $CH_2$, N, P and elements of Group 4 of the Periodic Table;
Y is O or OH;
k is 0, 1, or 2; and
l is 0, 1, or 2.

In one embodiment, said cyclic imide comprises N-hydroxyphthalimide.

In a further aspect, the present invention resides in a process for producing a phenol, said process comprising:

(a) contacting a reaction medium comprising an alkylaromatic compound of general formula (II):

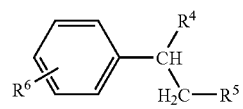

(II)

wherein $R^4$ and $R^5$ each independently represents hydrogen or an alkyl group having from 1 to 4 carbon atoms, provided that $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group, with oxygen in the presence of a catalyst comprising a cyclic imide of the general formula (I):

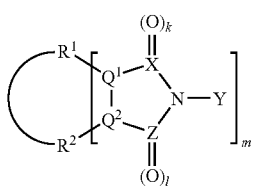

(I)

wherein each of $R^1$ and $R^2$ is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I, provided that $R^1$ and $R^2$ can be linked to one another via a covalent bond;
each of $Q^1$ and $Q^2$ is independently selected from C, CH, $CR^3$;
each of X and Z is independently selected from C, S, $CH_2$, N, P and elements of Group 4 of the Periodic Table;
Y is O or OH;
k is 0, 1, or 2;
l is 0, 1, or 2;

m is 1 to 3; and $R^3$ can be any of the entities (radicals, groups, or atoms) listed for $R^1$;

wherein said contacting produces an effluent comprising unreacted imide catalyst of said formula (I) and a hydroperoxide of general formula (IV):

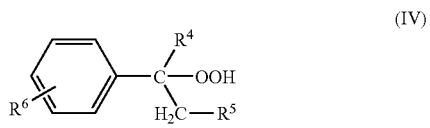

(IV)

in which $R^4$, $R^5$ and $R^6$ have the same meaning as in formula (II);

(b) treating the effluent with an aqueous solution of a metal carbonate or hydrogen carbonate to produce an aqueous phase comprising at least part of said unreacted imide catalyst of said formula (I) and an organic phase comprising said hydroperoxide of general formula (IV); and (c) recovering said organic phase; and (d) converting the hydroperoxide of formula (IV) from said organic phase into a phenol and an aldehyde or ketone of the general formula $R^4COCH_2R^5$ (V), in which $R^4$ and $R^5$ have the same meaning as in formula (II).

Conveniently, said contacting (a) is conducted at a temperature of between about 20° C. and about 150° C., such as between about 70° C. and about 130° C. The pressure at which the contacting (a) is conducted is conveniently between about 15 kPa and about 500 kPa, such as between 100 kPa to about 150 kPa.

Conveniently, said effluent is treated in (b) with an aqueous solution of a weak base having a pKb value greater than or equal to the pKa of the cyclic imide. In one embodiment, the base is a metal carbonate and/or hydrogen carbonate, for example an alkali metal carbonate and/or hydrogen carbonate, such as sodium carbonate.

Conveniently, the process further comprises acidifying said aqueous phase to precipitate said unreacted imide catalyst, optionally followed by recovering said precipitated unreacted imide catalyst and recycling the catalyst to (a).

DETAILED DESCRIPTION OF THE EMBODIMENTS

Figure 1:
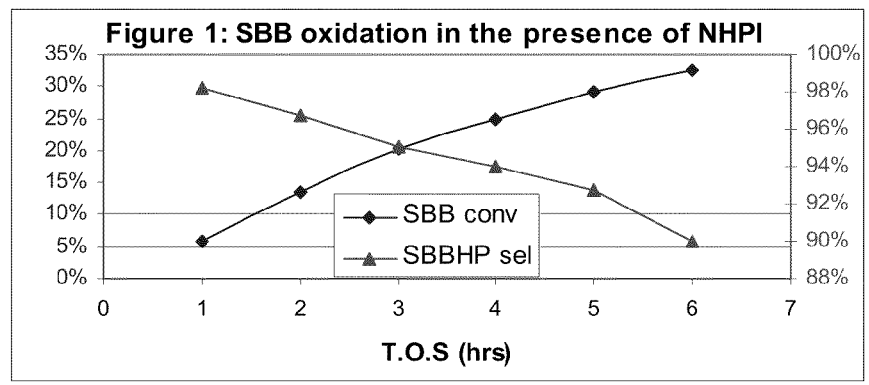
FIG. 1 is a graph plotting conversion and sec-butylbenzene hydroperoxide (SBBHP) selectivity against time on stream (T.O.S.) in the oxidation of sec-butylbenzene (SBB) in the presence of 0.46 wt % NHPI at 690 kPag (100 psig) according to the process of Example 1.

The terms "group," "radical," and "substituent" are used interchangeably in this document. For purposes of this disclosure, "hydrocarbyl radical" is defined to be a radical, which contains hydrogen atoms and up to 20 carbon atoms and which may be linear, branched, or cyclic, and when cyclic, aromatic or non-aromatic. "Substituted hydrocarbyl radicals" are radicals in which at least one hydrogen atom in a hydrocarbyl radical has been substituted with at least one functional group or where at least one non-hydrocarbon atom or group has been inserted within the hydrocarbyl radical. Conveniently, each of $R^1$ and $R^2$ is independently selected from aliphatic alkoxy or aromatic alkoxy radicals, carboxyl radicals, alkoxy-carbonyl radicals and hydrocarbon radicals, each of which radicals has 1 to 20 carbon atoms.

The present invention provides a process for oxidizing a hydrocarbon to at least one of the corresponding hydroperoxide, alcohol, ketone, carboxylic acid or dicarboxylic acid. The process comprises contacting a reaction medium comprising a hydrocarbon with an oxygen-containing gas in the presence of a catalyst comprising a cyclic imide of the general formula (I):

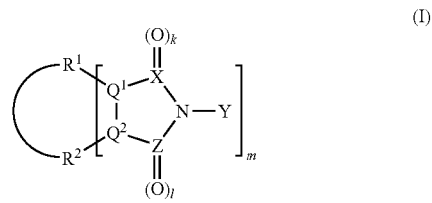

(I)

wherein each of $R^1$ and $R^2$ is independently selected from hydrocarbyl and substituted hydrocarbyl radicals having 1 to 20 carbon atoms, or the groups $SO_3H$, $NH_2$, OH and $NO_2$, or the atoms H, F, Cl, Br and I, provided that $R^1$ and $R^2$ can be linked to one another via a covalent bond; each of $Q^1$ and $Q^2$ is independently selected from C, CH, N and $CR^3$; each of X and Z is independently selected from C, S, $CH_2$, N, P and elements of Group 4 of the Periodic Table; Y is O or OH; k is 0, 1, or 2; l is 0, 1, or 2; m is 1 to 3; and $R^3$ can be any of the entities (radicals, groups, or atoms) listed for $R^1$. As used herein, the new numbering scheme for the Periodic Table Groups are employed as disclosed in Chemical and Engineering News, 63(5), 27 (1985).

The contacting produces an effluent comprising the desired oxidized hydrocarbon product together with unreacted imide catalyst of said formula (I). The effluent is then treated with an aqueous solution of a base so as to extract at least part of said unreacted imide catalyst from the effluent and produce an aqueous phase comprising the extracted imide catalyst and an organic phase comprising said oxidized hydrocarbon product. By acidifying the aqueous phase, the unreacted imide catalyst can be precipitated and recovered for possible recycle to the oxidation step.

Hydrocarbon Feed

Using the present process a wide group of substituted or unsubstituted saturated or unsaturated hydrocarbons, such as alkanes, cycloalkanes, alkenes, cycloalkenes, and aromatics, can be selectively oxidized. In particular, however, the process has utility in the selective oxidation of isobutane to tertiary butyl hydroperoxide and tertiary butanol, the selective oxidation of cyclohexane to cyclohexyl hydroperoxide, cyclohexanol and cyclohexanone and the selective oxidation to the corresponding hydroperoxides of alkylaromatic compounds of the general formula (II):

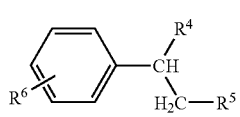

(II)

in which $R^4$ and $R^5$ each independently represents hydrogen or an alkyl group having from 1 to 4 carbon atoms, provided that $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group. In an embodiment, $R^4$ and $R^5$ are joined to form a cyclic group having from 4 to 10 carbon atoms, conveniently a cyclohexyl group, substituted with one or more alkyl group having from 1 to 4 carbon atoms or with one or more phenyl groups. Examples of suitable alkylaromatic compounds are ethyl benzene, cumene, sec-butylbenzene, sec-pentylbenzene, p-methyl-sec-butylbenzene, 1,4-diphenylcyclohexane, sec-hexylbenzene, and cyclohexylbenzene, with sec-butylbenzene and cyclohexylbenzene being preferred. It will also be understood that in the case where $R^1$ and $R^2$ are joined to form a cyclic group, the number of carbons forming the cyclic ring is from 4 to 10. However, that ring may itself carry one or more substituents, such as one or more alkyl groups having from 1 to 4 carbon atoms or one or more phenyl groups, as in the case of 1,4-diphenylcyclohexane.

In one practical embodiment, the alkylaromatic compound of general formula (II) is sec-butylbenzene and is produced by alkylating benzene with at least one $C_4$ alkylating agent under alkylation conditions and in the presence of a heterogeneous catalyst, such as zeolite Beta or more preferably at least one molecular sieve of the MCM-22 family (as defined below). The alkylation conditions conveniently include a temperature of from about 60° C. to about 260° C., for example between about 100° C. and about 200° C. The alkylation pressure is conveniently 7000 kPa or less, for example from about 1000 to about 3500 kPa. The alkylation is conveniently carried out at a weight hourly space velocity (WHSV) based on $C_4$ alkylating agent of between about 0.1 and about 50 $hr^{-1}$, for example between about 1 and about 10 $hr^{-1}$.

The $C_4$ alkylating agent conveniently comprises at least one linear butene, namely butene-1, butene-2 or a mixture thereof. The alkylating agent can also be an olefinic $C_4$ hydrocarbon mixture containing linear butenes, such as can be obtained by steam cracking of ethane, propane, butane, LPG and light naphthas, catalytic cracking of naphthas and other refinery feedstocks and by conversion of oxygenates, such as methanol, to lower olefins. For example, the following $C_4$ hydrocarbon mixtures are generally available in any refinery employing steam cracking to produce olefins and are suitable for use as the $C_4$ alkylating agent: a crude steam cracked butene stream, Raffinate-1 (the product remaining after solvent extraction or hydrogenation to remove butadiene from the crude steam cracked butene stream) and Raffinate-2 (the product remaining after removal of butadiene and isobutene from the crude steam cracked butene stream).

In a further practical embodiment, the alkylaromatic compound of general formula (II) is cyclohexylbenzene and is produced by contacting benzene with hydrogen in the presence of a heterogeneous bifunctional catalyst which comprises at least one metal having hydrogenation activity, typically selected from the group consisting of palladium, ruthenium, nickel and cobalt, and a crystalline inorganic oxide material having alkylation activity, typically at least one molecular sieve of the MCM-22 family (as defined below). The contacting step is conveniently conducted at a temperature of about 50° C. to about 350° C. The contacting pressure may be, for example, from about 100 to about 7000 kPa. The benzene to hydrogen molar ratio in the contacting step is preferably from about 0.01 to about 100. The WHSV during the contacting step is preferably in the range of about 0.01 to about 100.

The term "MCM-22 family material" (or "material of the MCM-22 family" or "molecular sieve of the MCM-22 family" or "MCM-22 family zeolite"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Molecular sieves of the MCM-22 family are preferred as the alkylation catalyst since they have been found to be highly selective to the production of sec-butylbenzene, as compared with the other butylbenzene isomers. Preferably, the molecular sieve is selected from (a) MCM-49, (b) MCM-56 and (c) isotypes of MCM-49 and MCM-56, such as ITQ-2.

Hydrocarbon Oxidation

The oxidation step in the present process is accomplished by contacting the hydrocarbon substrate with an oxygen-containing gas in the presence of a catalyst comprising a cyclic imide of the general formula (I):

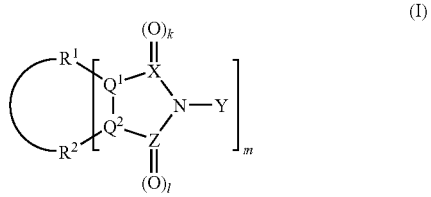

wherein each of $R^1$ and $R^2$ is independently selected from hydrocarbyl and substituted hydrocarbyl radicals having 1 to 20 carbon atoms, or the groups $SO_3H$, $NH_2$, $OH$ and $NO_2$, or the atoms H, F, Cl, Br and I provided that $R^1$ and $R^2$ can be linked to one another via a covalent bond; each of $Q^1$ and $Q^2$ is independently selected from C, CH, N and $CR^3$; each of X and Z is independently selected from C, S, $CH_2$, N, P and elements of Group 4 of the Periodic Table; Y is O or OH; k is 0, 1, or 2; l is 0, 1, or 2; m is 1 to 3 such as 1, 2 or 3, and $R^3$ can be any of the entities (radicals, groups, or atoms) listed for $R^1$. Conveniently, each of $R^1$ and $R^2$ is independently selected from aliphatic alkoxy or aromatic alkoxy radicals, carboxyl radicals, alkoxy-carbonyl radicals and hydrocarbon radicals, each of which radicals has 1 to 20 carbon atoms.

Generally, the cyclic imide employed as the oxidation catalyst obeys the general formula

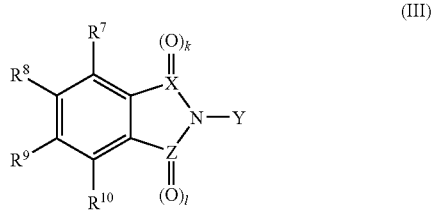

wherein each of $R^7$, $R^8$, $R^9$, and $R^{10}$ is independently selected from hydrocarbyl and substituted hydrocarbyl radicals having 1 to 20 carbon atoms, or the groups $SO_3H$, $NH_2$, $OH$ and $NO_2$, or the atoms H, F, Cl, Br and I; each of X and Z is independently selected from C, S, $CH_2$, N, P and elements of Group 4 of the Periodic Table; Y is O or OH; k is 0, 1, or 2, and l is 0, 1, or 2. Conveniently, each of $R^7$, $R^8$, $R^9$, and $R^{10}$ is independently selected from aliphatic alkoxy or aromatic alkoxy radicals, carboxyl radicals, alkoxy-carbonyl radicals and hydrocarbon radicals, each of which radicals has 1 to 20 carbon atoms.

In one practical embodiment, the cyclic imide catalyst comprises N-hydroxyphthalimide.

The conditions used to effect the oxidation step vary significantly with the type of hydrocarbon substrate to be oxidized, but generally suitable conditions include a temperature of between about 20° C. and about 150° C., such as between about 70° C. and about 130° C. The oxidation step is preferably carried out at a pressure between about 15 kPa and about 500 kPa, such as between 15 kPa to about 150 kPa.

Depending on the nature of the hydrocarbon substrate, the product of the oxidation step may include one or more of a hydroperoxide, alcohol, ketone, carboxylic acid or dicarboxylic acid of the corresponding hydrocarbon. In addition, however, the effluent from the oxidation process may contain unreacted cyclic imide catalyst in addition to the desired hydrocarbon oxidation product. Thus, according to the present process, the oxidation effluent is treated with an aqueous solution of a base, particularly a weak base having a pKb value greater than or equal to the pKa of the cyclic imide catalyst, whereby the unreacted imide catalyst is extracted into the aqueous phase, leaving an organic phase which comprises said oxidized hydrocarbon product and which contains a reduced level of cyclic imide. Generally, the extraction is conducted so as to reduce the level of the imide in the organic phase to less than 100 ppm, such as less than 50 ppm, for example less than 10 ppm, by weight of the organic phase. This is desirable not only because the imide is expensive but also because it can have deleterious effects on downstream operations such as hydroperoxide cleavage.

The use of a weak base in the extraction of the unreacted imide catalyst is generally desirable since a weak base is less likely to catalyze decomposition of the imide after extraction into the aqueous phase. A suitable weak base includes a metal carbonate and/or hydrogen carbonate, especially an alkali metal carbonate and/or hydrogen carbonate, such as sodium carbonate.

The conditions used in the cyclic imide extraction step need not be closely controlled but generally include a temperature of about 10° C. to about 80° C., such as about 20° C. to about 70° C. The time of extraction may be for example from about 1 minute to about 30 minutes, such as about 5 minutes to about 10 minutes. The amount of base employed in the extraction step is normally sufficient to provide at least an equimolar quantity of base to unreacted imide, such as 1 to 3 moles of base per mole of unreacted imide. Generally, the phases are agitated during extraction to maximize contact between the phases.

After extraction into the aqueous base solution, the unreacted cyclic imide can readily be recovered by acidifying the aqueous phase, for example with acetic acid, to precipitate the unreacted imide. After separation from the aqueous phase, for example by filtration or centrifugation, the precipitated unreacted imide may, if desired, be recycled to the oxidation step.

Oxidation Product

The product of the present oxidation process depends on the nature of the hydrocarbon substrate being oxidized but in general is a hydroperoxide, alcohol, ketone, carboxylic acid or dicarboxylic acid, especially a hydroperoxide.

For example, when the hydrocarbon substrate is isobutane, the oxidation product comprises tertiary butyl hydroperoxide (which is useful as an oxidation reagent and in the production of propylene oxide) and tertiary butanol (which is useful as a gasoline additive).

When the hydrocarbon substrate is cyclohexane, the oxidation product comprises cyclohexyl hydroperoxide, cyclohexanol and cyclohexanone. Cyclohexyl hydroperoxide is readily decomposed to additional cyclohexanol and cyclohexanone, either thermally or with the assistance of a catalyst. Cyclohexanol can be oxidized with aqueous nitric acid to produce adipic acid, which is a precursor in the synthesis of Nylon 6,6, whereas cyclohexanone can be converted to cyclohexanoxime which undergoes acid-catalyzed rearrangement to produce caprolactam, a precursor in the synthesis of Nylon 6.

Where the hydrocarbon substrate is an alkylaromatic compound of the general formula (II), the product of the oxidation reaction includes a hydroperoxide of general formula (IV):

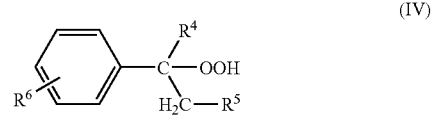

in which $R^4$, $R^5$ and $R^6$ have the same meaning as in formula (II). Preferably, the hydroperoxide is sec-butylbenzene hydroperoxide or cyclohexylbenzene hydroperoxide. This hydroperoxide can then be converted by acid cleavage to phenol or a substituted phenol and an aldehyde or ketone of the general formula $R^4COCH_2R^5$ (V), in which $R^4$ and $R^5$ have the same meaning as in formula (II). Phenol can of course be reacted with acetone to produce bisphenol A, a precursor in the production of polycarbonates and epoxy resins.

The hydroperoxide cleavage reaction is conveniently effected by contacting the hydroperoxide with a catalyst in the liquid phase at a temperature of about 20° C. to about 150° C., such as about 40° C. to about 120° C., and/or a pressure of about 50 to about 2500 kPa, such as about 100 to about 1000 kPa and/or a liquid hourly space velocity (LHSV) based on the hydroperoxide of about 0.1 to about 100 hr$^{-1}$, preferably about 1 to about 50 hr$^{-1}$. The hydroperoxide is preferably diluted in an organic solvent inert to the cleavage reaction, such as methyl ethyl ketone, phenol or sec-butylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid.

A suitable heterogeneous catalyst for use in the cleavage of sec-butylbenzene hydroperoxide includes a smectite clay, such as an acidic montmorillonite silica-alumina clay, as described in U.S. Pat. No. 4,870,217 (Texaco), the entire disclosure of which is incorporated herein by reference.

The invention will now be more particularly described with reference to the following non-limiting Examples.

EXAMPLE 1

Figure 2:
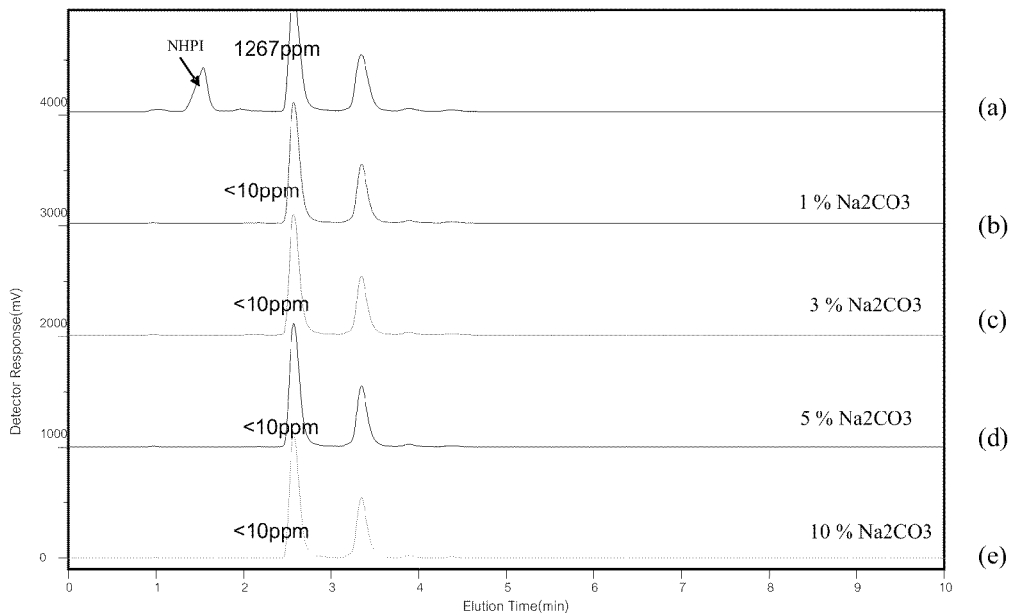
FIGS. 2(a) to (e) are high pressure liquid chromatography spectra of the effluent of the process of Example 1 without extraction [FIG. 2(a)] and of the organic phase remaining after extraction of the effluent with aqueous sodium carbonate solution of varying concentration [FIGS. 2(b) to (e)].
Figure 3:
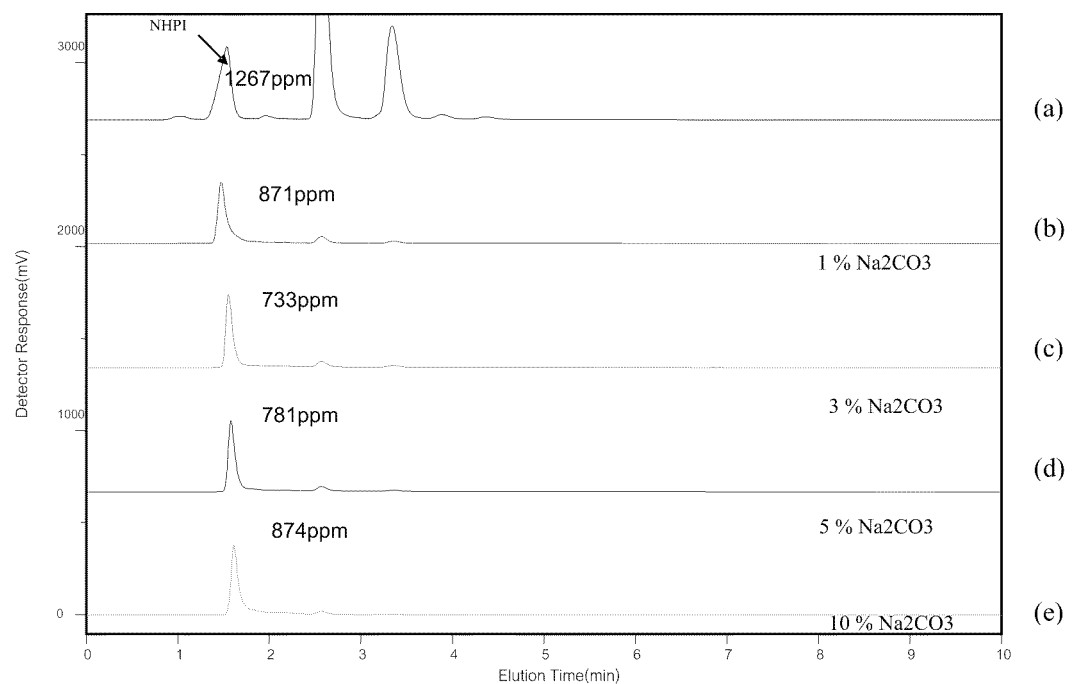
FIGS. 3(a) to (e) are high pressure liquid chromatography (HPLC) spectra of the effluent of the process of Example 1 without extraction [FIG. 3(a)] and of the aqueous phase produced after extraction of the effluent with aqueous sodium carbonate solutions of varying concentration [FIGS. 3(b) to (e)].

SBB Oxidation in the Presence of NHPI 150 gm of sec-butylbenzene (SBB) supplied by TCI America and 0.69 gm (0.46 wt %) of N-hydroxyphthalimide (NHPI) were weighed into a Parr reactor fitted with a stirrer, thermocouple, gas inlet, sampling port and a condenser containing a Dean Stark trap for water removal. The reactor and contents were stirred at 700 rpm and sparged with nitrogen at a flow rate of 250 cc/minute for 5 minutes. The reactor was then pressurized with nitrogen to 690 kPag (100 psig) while maintained under a nitrogen sparge and was then heated to 115° C. When the reaction temperature was reached, the gas was switched from nitrogen to air and the reactor was sparged with air at 250 cc/minute for 6 hours. Samples were taken hourly and the NHPI and acetic acid concentrations of each sample were measured by gas chromatography. After 6 hours, the gas was switched back to nitrogen and the heat was turned off. When the reactor had cooled, it was depressurized and the contents removed. The results are shown in FIG. 1. The NHPI content (in ppm by weight) of the oxidation product was measured using high pressure liquid chromatography (HPLC). The result is plotted in FIGS. 2 and 3 as the spectrum designated (a).

EXAMPLE 2

NHPI Removal from the Oxidation Mixture 5 gm of the oxidation product from example 1 was mixed at room temperature (25° C.) with 5 gm Na$_2$CO$_3$ aqueous solution containing 1 wt % of Na$_2$CO$_3$. The mixture (having a water/oxidation product mixture weight ratio of 1:1) was stirred with a magnetic stirrer bar for 5 minutes. The two layers were separated and the NHPI content (ppm by weight) in the organic and aqueous phases was analyzed by HPLC. The data are shown in FIG. 2(b) [organic phase] and FIG. 3(b) [aqueous phase]. The same procedure was carried out three separate times on 5 gm portions of the oxidation product of Example 1, but using 5 gm portions of three different Na$_2$CO$_3$ aqueous solutions containing 3 wt %, 5 wt % and 10 wt % of Na$_2$CO$_3$ respectively. The results are shown in FIGS. 2(c) and 3(c), FIGS. 2(d) and 3(d), and FIGS. 2(e) and 3(e) respectively. The data show that treating the oxidation product mixture with different concentration levels of a Na$_2$CO$_3$ solution is capable of removing substantially all of the NHPI and other byproducts from the oxidation product mixture.

In each case, the aqueous phase was acidified using acetic acid and the precipitated NHPI was recovered by filtration.

EXAMPLE 3

Extraction of NHPI with Aqueous Sodium Carbonate

Three batch sec-butylbenzene oxidation runs at the following conditions: 150 gr SBB, 500 ppm NHPI, temperature 125° C., atmospheric pressure, 250 cc/min air flow rate, were completed using N-hydroxyphalimide (NHPI) as the catalyst. The products were combined and analyzed for ppm NHPI and found to contain 494 ppm by high pressure liquid chromatography. The combined product mixtures were extracted with aqueous solutions of sodium carbonate at three molar ratios of NHPI to sodium carbonate (Carbonate/NHPI=1 to 1, 2 to 1 and 3 to 1). The following table indicates the results of these extractions. A second washing (extraction) was not required since the NHPI was not detectable (<10 ppm) in the organic phase after the first washing.

| Weight of Oxidation Products (g) | Millimoles of NHPI | Millimole of sodium carbonate | ml of sodium carbonate solution added | NHPI in Organic Phase (ppm) |
|---|---|---|---|---|
| 61.6 | 0.3776 | 0.3776 | 4.00 | <10 |
| 39.2 | 0.2403 | 0.4806 | 5.10 | <10 |
| 48.7 | 0.2985 | 0.8956 | 9.50 | <10 |

EXAMPLE 4

Extraction of NHPI from Concentrated SBBHP (72 wt %) with Aqueous Sodium Carbonate at 80° C.

A sec-butyl benzene oxidation batch run at the following conditions: 150 gr SBB, 1060 ppm NHPI, temperature 125° C., atmospheric pressure, 250 cc/min air flow rate was completed using N-hydroxyphalimide (NHPI) as the catalyst. The sec-butyl benzene conversion was 22 wt %. Sec-butyl benzene was removed by distillation under vacuum to obtain a concentrated solution containing 72.5 wt % of sec-butyl benzene hydroperoxide. The NHPI content was found to be 2144 ppm by high pressure liquid chromatography. 5 g of the concentrated solution was extracted with 5 g aqueous solution of sodium carbonate (3 wt %) at 80° C. The following table indicates the result of this extraction. A second washing (extraction) was not required since the NHPI was not detectable (<10 ppm) in the organic phase after the first washing. Gas chromatographic analysis showed sec-butyl benzene hydroperoxide (SBBHP) at this concentration and at this temperature to be thermally and chemically stable.

|  | NHPI ppm | SBBHP wt % |
|---|---|---|
| Before extraction | 2144 | 72.44 |
| After extraction | <10 | 72.9 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for oxidizing a hydrocarbon, the process comprising:
   (a) contacting a hydrocarbon with an oxygen-containing gas in the presence of a catalyst comprising a cyclic imide of the general formula (I):

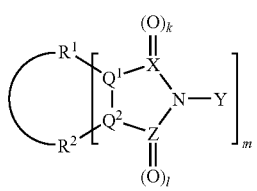

(I)

wherein each of $R^1$ and $R^2$ is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I, provided that $R^1$ and $R^2$ can be linked to one another via a covalent bond;
each of $Q^1$ and $Q^2$ is independently selected from C, CH, N and $CR^3$;
each of X and Z is independently selected from C, S, $CH_2$, N, P and elements of Group 4 of the Periodic Table;
Y is O or OH;
k is 0, 1, or 2;
l is 0, 1, or 2;
m is 1 to 3; and
$R^3$ is any of the entities listed for $R^1$;
to produce an effluent comprising an oxidized hydrocarbon product and unreacted imide catalyst of formula (I);
   (b) treating the effluent with an aqueous solution of a base to produce an aqueous phase comprising at least part of the unreacted imide catalyst of formula (I) and an organic phase comprising the oxidized hydrocarbon product; and
   (c) recovering the organic phase.

2. The process of claim 1, wherein said cyclic imide is of the general formula (III):

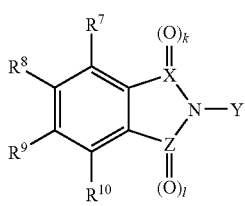

(III)

wherein each of $R^7$, $R^8$, $R^9$, and $R^{10}$ is independently selected from hydrocarbyl and substituted hydrocarbyl radicals having 1 to 20 carbon atoms, or from the groups $SO_3H$, $NH_2$, OH and $NO_2$, or from the atoms H, F, Cl, Br and I;
each of X and Z is independently selected from C, S, $CH_2$, N, P and elements of Group 4 of the Periodic Table;
Y is O or OH,
k is 0, 1, or 2, and
l is 0, 1, or 2.

3. The process of claim 1, wherein the cyclic imide is N-hydroxyphthalimide.

4. The process of claim 1, wherein contacting (a) is conducted at a temperature of between 20° C. and 150° C.

5. The process of claim 4, wherein the temperature is between 70° C. and 130° C.

6. The process of claim 1, wherein contacting (a) is conducted at a pressure between 15 kPa and 500 kPa.

7. The process of claim 6, wherein the pressure is between 15 kPa and 150 kPa.

8. The process of claim 1, wherein the effluent is treated in (b) with an aqueous solution of a weak base having a pKb value greater than or equal to the pKa value of the cyclic imide.

9. The process of claim 1, wherein the effluent is treated in (b) with an aqueous solution of a metal carbonate and/or hydrogen carbonate.

10. The process of claim 9, wherein the effluent is treated in (b) with an aqueous solution of an alkali metal carbonate and/or hydrogen carbonate.

11. The process of claim 10, wherein the effluent is treated in (b) with an aqueous solution of sodium carbonate.

12. The process of claim 1 and further comprising acidifying the aqueous phase to precipitate the unreacted imide catalyst.

13. The process of claim 12 and further comprising recovering the precipitated unreacted imide catalyst and recycling the catalyst to (a).

14. The process of claim 1, wherein the hydrocarbon comprises an alkane or cycloalkane.

15. The process of claim 14, wherein the hydrocarbon comprises isobutane or cyclohexane.

16. The process of claim 15, wherein the hydrocarbon comprises cyclohexane, the organic phase recovered in (c) comprises cyclohexanol and the process further comprises converting the cyclohexanol to adipic acid.

17. The process of claim 15, wherein the hydrocarbon comprises cyclohexane, the organic phase recovered in (c) comprises cyclohexanone and the process further comprises converting the cyclohexanone to caprolactam.

18. The process of claim 15, wherein the hydrocarbon comprises iso-butane, the organic phase recovered in (c) comprises tert-butyl hydroperoxide and the process further comprises using the tert-butyl hydroperoxide as an oxidation catalyst.

19. The process of claim 1, wherein the hydrocarbon comprises an alkylaromatic compound of general formula (II):

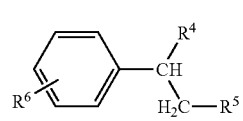

(II)

wherein $R^4$ and $R^5$ each independently represents hydrogen or an alkyl group having from 1 to 4 carbon atoms, provided that $R^4$ and $R^5$ may be joined to form a cyclic group having from 4 to 10 carbon atoms, said cyclic group being optionally substituted, and $R^6$ represents hydrogen, one or more alkyl groups having from 1 to 4 carbon atoms or a cyclohexyl group, and wherein the oxidized hydrocarbon product comprises a hydroperoxide of general formula (IV):

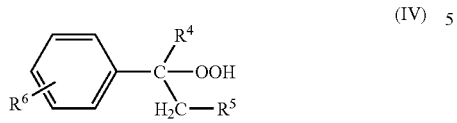

in which $R^4$, $R^5$ and $R^6$ have the same meaning as in formula (II).

20. The process of claim 19 and further comprising converting the hydroperoxide of formula (IV) from the organic phase into a phenol and an aldehyde or ketone of the general formula $R^4COCH_2R^5$ (V), in which $R^4$ and $R^5$ have the same meaning as in formula (II).

21. The process of claim 19, wherein the alkylaromatic compound of general formula (II) is selected from ethyl benzene, cumene, sec-butylbenzene, sec-pentylbenzene, p-methyl-sec-butylbenzene, 1,4-diphenylcyclohexane, sec-hexylbenzene, and cyclohexylbenzene.

22. The process of claim 21, wherein the alkylaromatic compound is sec-butylbenzene or cyclohexylbenzene.

23. The process of claim 20 and further comprising converting the phenol produced into bisphenol A.

24. The process of claim 1, wherein each of the $Q^1$ and the $Q^2$ is independently selected from C, CH, and $CR^3$.

* * * * *

UNITED STATES PATENT AND TRADEMARK OFFICE
CERTIFICATE OF CORRECTION

PATENT NO.       : 8,487,138 B2                                                                                  Page 1 of 1
APPLICATION NO. : 12/601549
DATED            : July 16, 2013
INVENTOR(S)      : Dakka et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 465 days.

Signed and Sealed this
Eighth Day of September, 2015

Michelle K. Lee
*Director of the United States Patent and Trademark Office*